United States Patent [19]

Kis-Tamás et al.

[11] Patent Number: 4,740,228
[45] Date of Patent: Apr. 26, 1988

[54] PLANT GROWTH REGULATING COMPOUNDS AND COMPOSITIONS AND A PROCESS FOR THE PREPARATION THEREOF

[75] Inventors: Attila Kis-Tamás; Ferenc Jurák; Zoltán Vig; Pál Fekete; Judit Kulcsár, all of Budapest, Hungary

[73] Assignee: Egyt Gyogyszervegyeszeti Gyar, Budapest, Hungary

[21] Appl. No.: 569,594

[22] Filed: Jan. 10, 1984

Related U.S. Application Data

[63] Continuation of Ser. No. 238,979, Feb. 27, 1981, abandoned.

[30] Foreign Application Priority Data

Feb. 29, 1980 [HU] Hungary ............... 464/80

[51] Int. Cl.[4] ............... A01N 37/22; A01N 37/20
[52] U.S. Cl. ................... 71/77; 71/88; 71/94; 71/95; 71/105; 558/404; 544/163; 546/226; 548/540; 540/607
[58] Field of Search ............... 71/105, 118, 77; 558/404

[56] References Cited

U.S. PATENT DOCUMENTS

| | | | |
|---|---|---|---|
| 2,412,510 | 12/1946 | Jones | 71/118 |
| 3,020,146 | 2/1962 | Richter | 71/118 |
| 3,472,646 | 10/1969 | Eue et al. | 71/118 |
| 4,239,528 | 12/1980 | Schröder et al. | 71/105 |
| 4,261,731 | 4/1981 | Schröder et al. | 71/105 |
| 4,313,754 | 2/1982 | Szucs | 71/105 |

FOREIGN PATENT DOCUMENTS

| | | | |
|---|---|---|---|
| 53-53617 | 5/1978 | Japan | 71/105 |
| 1170653 | 11/1969 | United Kingdom | 71/118 |

OTHER PUBLICATIONS

Boon et al., "Some Derivatives, etc.," (1954), J. Chem. Soc., 1954, pp. 3263–3272, (1954).
Shimo et al., "Solvent–Catalyzed Alkylations, etc.," (1961), J. Org. Chem., 26, pp. 4868–4871, (1961).

Primary Examiner—Glennon H. Hollrah
Assistant Examiner—Amelia A. Owens
Attorney, Agent, or Firm—Keil & Weinkauf

[57] ABSTRACT

The invention relates to new plant growth regulating compositions, which contain as active agent 0.001 to 95% by weight of one or more compound(s) of the general formula (I),

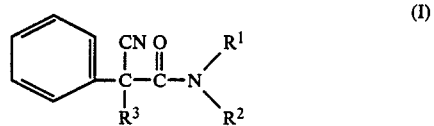
(I)

wherein
$R^1$ and $R^2$ each represent hydrogen atom, a $C_{1-5}$ alkyl group, a $C_{5-7}$ cycloalkyl group, an aryl group, a halogen-substituted aryl group, an aralkyl group, a $C_{2-5}$ alkenyl group or a $C_{2-5}$ alkynyl group, or
$R^1$ and $R^2$ form, together with the adjacent nitrogen atom, a morpholino, pyrrolidino, piperidino or perhydroazepinyl group, and
$R^3$ stands for hydrogen or a $C_{1-5}$ alkyl group, together with an inert, solid, liquid and/or gaseous carrier or diluent, and optionally one or more additives, such as surfactants or other substances of plant biological activity.

The compounds of the general formula (I) in which $R^1$ is hydrogen and $R^2$ stands for hydrogen, $C_{1-3}$ alkyl, aralkyl or $C_{3-5}$ alkenyl group, furthermore in which $R^1$ and $R^3$ are hydrogen and $R^2$ is an aryl group have already been described in the literature, whereas the remaining derivatives of the general formula (I) are new. These compounds can be prepared by reacting a compound of the general formula (II)

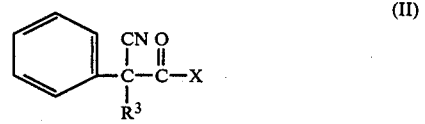

(II)

with an amine of the general formula (III),

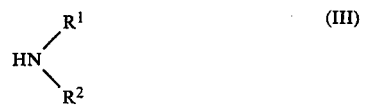
(III)

or by alkylating a compound of the general formula (IV).

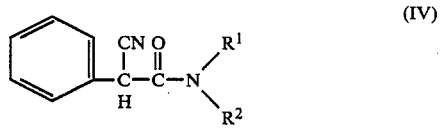

(IV)

In the above formulae X stands for halogen, hydroxy or $C_{1-4}$ alkoxy, whereas $R^1$, $R^2$ and $R^3$ have the meanings as defined above.

11 Claims, No Drawings

PLANT GROWTH REGULATING COMPOUNDS AND COMPOSITIONS AND A PROCESS FOR THE PREPARATION THEREOF

This is a continuation of application Ser. No. 238,979, filed Feb. 27, 1981, now abandoned.

The invention relates to new agricultural compositions with plant growth regulating effects. The invention also relates to new phenylacetic acid derivatives which can be applied as active agents in the new compositions, as well as to a process for the preparation of the new compounds.

Plant growth regulating agents have been applied in the agriculture and horticulture for about 40–50 years. The known plant growth regulating agents can be classified into two groups, i.e. naturally occurring substances and compounds prepared by chemical synthesis.

Of the naturally occurring substances e.g. auxines, gibberellines and abscissic acids are to be mentioned [Wegler, R.: Chemie der Pflanzenschutz- und Schädlingsbekämpfungsmittel, p. 399–429, Springer Verlag (1970)]. Since these substances do generally not meet the requirements of practical utilization, an extensive research work has been initiated to prepare synthetic substances with plant growth regulating effects [Wegler, R.: Chemie der Pflanzenschutz- und Schädlingsbekämpfungsmittel, Vol. 4, p. 47–48, Springer Verlag (1977)].

The majority of the synthetic substances with plant growth regulating effects has the disadvantage that they can be applied only on a rather restricted field under strictly defined conditions, or else significant undesired side effects occur upon their application.

The invention aims at the elaboration of new compositions with plant growth regulating effects, which exert no or only slight undesired side effects (deformations, killing).

In one aspect, the invention relates to a plant growth regulating condition, characterized by containing as active agent 0.001 to 95% by weight of one or more compound(s) of the general formula (I),

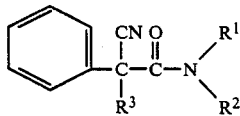

(I)

wherein
$R^1$ and $R^2$ each represent hydrogen atom, a $C_{1-5}$ alkyl group, a $C_{5-7}$ cycloalkyl group, an aryl group, a halogen-substituted aryl group, an aralkyl group, a $C_{2-5}$ alkenyl group or a $C_{2-5}$ alkynyl group, or
$R^1$ and $R^2$ form, together with the adjacent nitrogen atom, a morpholino, pyrrolidino, piperidino or perhydroazepinyl group, and
$R^3$ stands for hydrogen or a $C_{1-5}$ alkyl group,
together with an inert solid, liquid and/or gaseous carrier or diluent, and optionally one or more additives, such as surfactants or other substances of plant biological activity.

The invention is based on the recognition that the compounds of the general formula (I) exert surprising and valuable effects in the field of plant protection.

The compositions according to the invention are effective both in the vegetative and in the generative phases of plant growth, thus they can be applied not only to stimulate plant growth but, depending on the manner of application, to increase crop yield as well in relatively low doses.

It is known that most of the plant growth stimulating substances exert herbicidal effects in higher doses [Brown, B. T.: Pest. Sci. 3, 161 (1971)]. If the plant growth stimulating dose of a substance is close to the herbicidal dose, it can be applied to regulate plant growth only with great difficulties, if at all. A great advantage of the compositions according to the invention is that they do not damage cultivated plants in doses five or even ten times higher than the plant growth stimulating dose. A further advantage of the new compounds having the general formula (I) is that they are non-toxic or warm-blooded organisms, or their toxicity is extremely low. As an additional advantage, the new compounds of the general formula (I) can be prepared simply and economically even on large scale.

The new compositions according to the invention exert their plant growth regulating effects upon both pre-emergent and post-emergent applications. The compositions can be applied to advantage to accelerate the growth of e.g. maize, sunflower, tomato, soybean and bean.

The plant growth regulating compositions according to the invention can be prepared by methods well known in the field of plant protection, and can be formulated into compositions commonly applied for this purpose.

As mentioned above, the plant growth regulating compositions according to the invention contain, in addition to the active ingredient of the general formula (I), conventional carriers and/or diluents, optionally together with conventional additives, such as dispersing agents, surfactants, substances which regulate the duration of effect, adhesion-increasing agents, etc.

The compositions according to the invention can be presented preferably in the form of wettable powders (WP). The wettable powders can be prepared so that the active agent, powdered to a particle size of 1 to $20\mu$ in a conventional grinding apparatus, is admixed with one or more conventional carrier(s), e.g. dolomite, kaoline, diatomaceous earth, etc., ionic or non-ionic wetting agents [such as quaternary ammonium salts containing one or two higher alkyl group(s), Arkopon T (sodium oleyl tauride), various wetting agents of the Atlox group, condensation products of ethylene oxide and lower alkylphenols, etc.], and optionally with other additives, such as dispersing agents (e.g. powdery sulfite waste liquor), adhesion-increasing substances (e.g. waxes, powdered whey), etc. The resulting wettable powders with an active agent content of about 20 to 90% by weight, preferably 50 to 90% by weight, can be diluted with water to obtain spray liquids which can be applied directly for the pre-emergent or post-emergent treatment of plants. These spray liquids contain about 0.01 to 10% by weight, preferably about 0.1 to 1.0% by weight, of the active agent.

Several representatives of the new compounds having the general formula (I) are soluble in water. These compounds can be admixed with a small amount of a wetting agent and then dissolved in water, to obtain a spray solution without utilizing any further diluent. If desired, one or more adhesion-increasing substance(s) can also be added to these spray solutions.

The new compositions according to the invention can also be presented in the form of emulsifiable concentrates (EC) or colloidal suspensions (Coll.). These compositions are prepared so that the active agent of the general formula (I) is dissolved or suspended in a water-immiscible organic solvent, such as xylene, petrol, isophorone, rape oil, etc. An ionic or non-ionic surfactant, thus e.g. a wetting agent mentioned in connection with the preparation of wettable powders, is added then, in an amount required to obtain a stable emulsion, to the resulting concentrate with an active agent content of generally about 10 to 50% by weight. The resulting emulsifiable concentrates can be diluted with water to obtain a spray liquid ready for use, containing generally 0.01 to 1.0% by weight of the active agent.

The compositions can also be presented in microgranular form. These microgranules are prepared by impregnating a granular support (such as dolomite, pearlite, coke, granulated corn cob, etc.; particle size: about 0.1 to 1 mm) with a solution of the active agent in an appropriate organic solvent, and then removing the solvent. The resulting microgranules are applied onto the area to be treated by means of a conventional spreading apparatus.

The microgranules can also be prepared according to the classical wet granulation method, by admixing the active agent and the diluents, granulating the resulting wet mass, drying the granules, and separating the fraction with the appropriate particle size by sieving. The granules can be applied onto the area to be treated by means of a conventional spreading apparatus.

The compositions according to the invention enhance germination and favourably influence the development of plants. For this purpuse the appropriately formulated active agent is applied onto the surface of seeds e.g. by film coating or seed dressing techniques. Seed dressing can be performed by conventional methods, utilizing a spray liquid prepared from a wettable powder, emulsifiable concentrate or colloidal suspension of the active agent. According to a preferred method a film-forming agent, such as gelatine, starch derivatives, ultraamylopectine, etc., is also added to the spray liquid, and the active agent is applied onto the seed surface as a film coating.

The compositions according to the invention may also contain, in addition to the active agents of the general formula (I), known fungicidal, insecticidal or wild animal-repellent agents. For this purpose e.g. TMTD (tetramethyl-thiuram-disulfide), captan (N-trichloromethylthiotetrahydrophthalimide), malathion [O,O-diethyl-S-(1,2-dicarbethoxyethyl)-dithiophosphate] and methiocarb (3,5-dimethyl-4-methylmercaptophenyl-N-methyl-carbamate) can be applied.

The majority of the compounds having the general formula (I) are new. Some representatives of the compounds having the general formula (I), i.e. those in which $R^1$ is hydrogen and $R^2$ stands for hydrogen, $C_{1-3}$ alkyl group, aralkyl group or a $C_{3-5}$ alkenyl group, furthermore those in which $R^1$ and $R^3$ each represent hydrogen and $R^2$ stands for aryl group, have already been described in the literature [see J. Chem. Soc. 1954, 3263; British patent specification No. 309,508; J. Org. Chem. 23, 504; J. Org. Chem. 26, 4868; J. Am. Chem. Soc. 47, 875; Chem. Abstr. 58, 7827c; 53, 6100a; 55, 27201c; 47, 3243i; 59, 2806h; 62, P 14636g; 17, P 1802; 63, P 14878k].

No mention is made, however, in the above reference of the possible plant biological effects of the compounds in question.

In a second aspect, the invention relates to new compounds of the general formula (I), wherein $R^1$, $R^2$ and $R^3$ are as defined above, with the proviso that (i) if $R^1$ is hydrogen, $R^2$ may not stand for hydrogen, $C_{1-3}$ alkyl, aralkyl or $C_{3-5}$ alkenyl, or (ii) if both $R^1$ and $R^3$ are hydrogen, $R^2$ may not stand for aryl.

The term "aryl group" as used in the specification and in the claims denotes the phenyl and naphthyl groups. The aryl groups may be unsubstituted or may have one or more halogen substituents [fluorine, chlorine, bromine and/or iodine atoms, particularly chlorine atom(s)]. Of the halogen-substituted aryl groups e.g, the 2-chloro-, 4-chloro-, 2,4-dichloro-, 2,3-dichloro- and 3,4-dichlorophenyl groups are to be mentioned. The term "aralkyl group" refers to $C_{1-4}$ alkyl groups having one or more aryl substituent(s) as defined above (such as benzyl, phenethyl, $\beta,\beta$-diphenylethyl, etc. groups). Preferred representatives of the $C_{2-5}$ alkenyl groups are the vinyl and allyl groups, whereas of the $C_{2-5}$ alkynyl groups the propargyl group is preferred. Preferred representatives of the alkyl groups are the methyl, ethyl, n-propyl, isopropyl and n-butyl groups, whereas of the $C_{5-7}$ cycloalkyl groups the cyclopentyl and cyclohexyl groups and preferred.

Preferred representatives of the active agents having the general formula (I) are those compounds in which $R^1$ stands for hydrogen, $C_{1-3}$ alkyl, benzyl or allyl, $R^2$ is hydrogen, $C_{1-3}$ alkyl or allyl, or $R^1$ and $R^2$ form, together with the adjacent nitrogen atom, a perhydroazepinyl or a morpholino group, and $R^3$ is a $C_{1-3}$ alkyl group.

Particularly preferred representatives of the active agents having the general formula (I) are those in which $R^1$ is hydrogen, methyl, ethyl, n-propyl, isopropyl or benzyl, $R^2$ is hydrogen, methyl or allyl, or $R^1$ and $R^2$ form, together with the adjacent nitrogen atom, a perhydroazepinyl or a morpholino group, and $R^3$ is ethyl.

The invention relates further to a process for the preparation of new compounds having the general formula (I), wherein $R^1$, $R^2$ and $R^3$ are as defined above, with the proviso that (i) if $R^1$ is hydrogen, $R^2$ may not stand for hydrogen, $C_{1-3}$ alkyl, aralkyl or $C_{3-5}$ alkenyl, or (ii) if both $R^1$ and $R^3$ are hydrogen, $R^2$ may not stand for aryl.

These compounds are prepared according to the invention so that (a) a compound of the general formula (II),

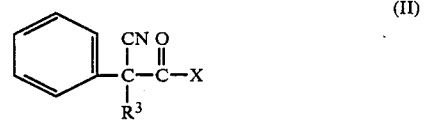

(II)

wherein $R^3$ is as defined above and X stands for halogen, hydroxy or $C_{1-4}$ alkoxy, is reacted with an amine of the general formula (III),

(III)

wherein $R^1$ and $R^2$ are as defined above, or (b) to prepare a compound of the general formula (I) in which $R^3$ stands for a $C_{1-5}$ alkyl group, a compound of the general formula (IV),

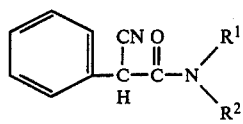

(IV)

wherein $R^1$ and $R^2$ are as defined above, is alkylated.

Process variant (a) can be performed in numerous ways. One can proceed e.g. so that a compound of the general formula (II) in which X is a $C_{1-4}$ alkoxy group is applied as starting substance, and the reaction is performed in an organic solvent medium. As reaction medium protic organic solvents, preferably alcohols (such as methanol or ethanol), or less protic non-polar solvents, such as benzene or toluene, can be applied. The reaction can be performed at temperatures ranging from room temperature to the boiling point of the mixture, sometimes, however, it is more preferred to perform the reaction under cooling, e.g. at 5° to 10° C. According to a preferred method a catalyst, such as pyridine, is also added to the reaction mixture. The reaction mixture can be processed by conventional methods, such as cooling, filtering, evaporation, etc.

The starting substances of the general formula (II) in which X is an alkoxy group can be prepared according to methods described in the literature, by reacting benzyl cyanide with a dialkyl carbonate (Org. Synth. Coll. Vol. IV, 461), and alkylating the resulting compound with an alkyl halide, if necessary.

Process variant (a) of the invention can also be performed so that a compound of the general formula (II) in which X is halogen, preferably chlorine or bromine, is applied as starting substance. The reaction can be performed in the presence of an organic solvent. As reaction medium non-polar organic solvents, preferably chloroform, dichloromethane, methylene chloride, benzene or benzene homologues (such as toluene) can be applied. The reaction is performed preferably in the presence of an acid binding agent. For this purpose an organic base, such as triethylamine or pyridine, or an inorganic base, such as sodium hydroxide, sodium carbonate, potassium hydrocarbonate, etc., can be added to the reaction mixture, an excess of the amine reactant of the general formula (III) can, however, also serve as acid binding agent. The reaction temperature ranges from about $-10°$ C. to the boiling point of the mixture.

The starting substances of the general formula (II) in which X is halogen can be prepared by subjecting the respective esters of the general formula (II) (X=alkoxy) to hydrolysis, and treating the resulting carboxylic acid with an inorganic alkyl halide, such as phosphorous pentachloride (Bull. Soc. Chim. Fr. 1959, 1641).

Process variant (a) of the invention can also be performed by applying a free acid, i.e. a compound of the general formula (II) wherein X is hydroxy, as starting substance. This method, like the first variant in which the starting substance is an ester, can be applied to advantage for the preparation of compounds of the general formula (I) in which $R^1$ is hydrogen. Compounds of the general formula (I) in which $R^1$ is other than hydrogen can be prepared preferably by applying an acyl halide of the general formula (II) as starting substance.

The reaction of a free carboxylic acid of the general formula (II) (X=hydroxy) and an amine of the general formula (III) can be performed preferably in the presence of a dehydrating agent. Conventional condensing agents, such as dicyclohexyl carbodiimide, can be applied for this purpose.

According to process variant (b) of the invention a compound of the general formula (IV) is alkylated. Alkylation is performed by methods well known in the art (see e.g. J. Am. Chem. Soc. 47, 875; J. Org. Chem. 26, 4868; J. Org. Chem. 28, 504), by applying preferably an alkyl halide, such as methyl iodide, methyl chloride, ethyl chloride, ethyl bromide, etc., or a dialkyl sulfate, e.g. diethyl sulfate, as alkylating agent. According to a preferred method the starting substance of the general formula (IV) is converted first into its alkali metal derivative. This reaction can be performed with the respective alkali metal alkoxide in an alkanol medium, e.g. with sodium ethoxide in ethanol. The resulting alkali metal derivative can be then reacted directly, i.e. without isolation, with the respective alkyl halide or dialkyl sulfate.

The plant growth regulating effects of the compounds having the general formula (I) are demonstrated by the results of the following tests.

Test 1: Laboratory testing of the compounds embedded into sand

River sand is washed twice with water and then distributed into Petri dishes. The sand portions are then admixed with a solution or suspension of the test compound formed with 10 ml of acetone, the solvent is allowed to evaporate, and then 20 corn seeds, 20 sunflower seeds or 40 tomato seeds are down into the individual Petri dishes. The compounds are tested in three different concentrations corresponding to an application rate of 0.1, 1 and 10 lb/acre (0.1, 1 and 10 kg/hectare), respectively, and the individual tests are repeated four times. A temperature of 22° C. in average is maintained during the test period. The rate of germination is determined on the 8th day, whereas the height of the plants is measured on the 15th day. The results are summarized in Table 1.

Test 2: Greenhouse tests on soil 50 g of forest humus soil are filled into Petri dishes in more layers, the soil surface is levelled, and 1 g of soil, containing the test compound in a concentration corresponding to an application rate of 1, 3 or 5 kg/hectare, respectively, is spread onto it. Seeds of corn, soybean and sunflower are sown into the soil, and the seeds are covered with a further soil layer.

24 ml of distilled water are filled into each of the Petri dishes, thereafter the Petri dishes are closed until the seedlings emerge. The humidity content of the soil is 30% throughout the test period, and the temperature is maintained at 21° C. The results are evaluated on the 21st day by measuring the height, determining the germination ratio and measuring the dry weight of the plants. The results are listed in Tables 2 to 10 as the averages of five parallel tests.

The figures given in Tables 1 to 10 represent the results in relation to the untreated controls according to the following scale:

5: over 110% related to the untreated controls
4: 100 to 110% related to the untreated controls
3: 100% related to the untreated controls
2: 90 to 100% related to the untreated controls
1: 75 to 90% related to the untreated controls

TABLE 1

| R³ | R¹ | R² | Test plant | Test | Dose, kg/ha | | |
|---|---|---|---|---|---|---|---|
| | | | | | 0.1 | 1 | 10 |
| ethyl | n-propyl | hydrogen | maize | germination, % | 4 | 3 | 2 |
| | | | | height (% of the control) | 4 | 5 | 2 |
| | | | sunflower | germination, % | 4 | 4 | 2 |
| | | | | height (% of the control) | 4 | 5 | 2 |
| | | | tomato | germination, % | 4 | 4 | 2 |
| | | | | height (% of the control) | 4 | 5 | 2 |

TABLE 2

| R³ | R¹ | R² | Test plant | Test | | Dose, kg/ha | | |
|---|---|---|---|---|---|---|---|---|
| | | | | | | 1 | 3 | 5 |
| ethyl | isopropyl | hydrogen | maize | pre-emergent | Germination, % | 4 | 4 | 2 |
| | | | | | Height (% of the control) | 2 | 4 | 4 |
| | | | | | Dry weight (% of the control) | 4 | 3 | 3 |
| | | | | post-emergent | Germination, % | 5 | 4 | 4 |
| | | | | | Height (% of the control) | 4 | 4 | 4 |
| | | | | | Dry weight (% of the control) | 5 | 4 | 5 |
| | | | sunflower | pre-emergent | Germination, % | 4 | 4 | 5 |
| | | | | | Height (% of the control) | 5 | 5 | 5 |
| | | | | | Dry weight (% of the control) | 5 | 5 | 5 |
| | | | | post-emergent | Germination, % | 4 | 2 | 2 |
| | | | | | Height (% of the control) | 4 | 4 | 5 |
| | | | | | Dry weight (% of the control) | 5 | 4 | 4 |
| ethyl | isopropyl | hydrogen | soybean | pre-emergent | Germination, % | 4 | 4 | 4 |
| | | | | | Height (% of the control) | 4 | 4 | 4 |
| | | | | | Dry weight (% of the control) | 5 | 4 | 4 |
| | | | | post-emergent | Germination, % | 3 | 4 | 2 |
| | | | | | Height (% of the control) | 2 | 4 | 4 |
| | | | | | Dry weight (% of the control) | 2 | 4 | 2 |

TABLE 3

| R³ | R¹ | R² | Test plant | Test | | Dose, kg/ha | | |
|---|---|---|---|---|---|---|---|---|
| | | | | | | 1 | 3 | 5 |
| ethyl | benzyl | hydrogen | maize | pre-emergent | Germination, % | 4 | 4 | 4 |
| | | | | | Height (% of the control) | 4 | 4 | 4 |
| | | | | | Dry weight (% of the control) | 4 | 2 | 2 |
| | | | | post-emergent | Germination, % | 4 | 4 | 2 |
| | | | | | Height (% of the control) | 4 | 4 | 2 |
| | | | | | Dry weight (% of the control) | 5 | 5 | 2 |
| | | | sunflower | pre-emergent | Germination, % | 5 | 4 | 4 |
| | | | | | Height (% of the control) | 5 | 5 | 5 |
| | | | | | Dry weight (% of the control) | 5 | 5 | 5 |
| | | | | post-emergent | Germination, % | 4 | 4 | 2 |
| | | | | | Height (% of the control) | 4 | 5 | 4 |
| | | | | | Dry weight (% of the control) | 4 | 4 | 2 |
| ethyl | benzyl | hydrogen | soybean | pre-emergent | Germination, % | 4 | 4 | 4 |
| | | | | | Height (% of the control) | 4 | 4 | 4 |
| | | | | | Dry weight (% of the control) | 4 | 4 | 2 |
| | | | | post-emergent | Germination, % | 2 | 4 | 2 |
| | | | | | Height (% of the control) | 4 | 4 | 4 |
| | | | | | Dry weight (% of the control) | | | |

TABLE 4

| R³ | R¹ | R² | Test plant | Test | | Dose, kg/ha | | |
|---|---|---|---|---|---|---|---|---|
| | | | | | | 1 | 3 | 5 |
| ethyl | n-propyl | hydrogen | maize | pre-emergent | Germination, % | 4 | 4 | 4 |
| | | | | | Height (% of the control) | 4 | 2 | 2 |
| | | | | | Dry weight (% of the control) | 4 | 2 | 2 |
| | | | | post-emergent | Germination, % | 5 | 4 | 4 |
| | | | | | Height (% of the control) | 2 | 2 | 2 |
| | | | | | Dry weight (% of the control) | 4 | 4 | 4 |
| | | | sunflower | pre-emergent | Germination, % | 5 | 4 | 4 |
| | | | | | Height (% of the control) | 5 | 5 | 5 |
| | | | | | Dry weight (% of the control) | 5 | 5 | 5 |
| | | | | post-emergent | Germination, % | 3 | 4 | 3 |
| | | | | | Height (% of the control) | 5 | 4 | 5 |
| | | | | | Dry weight (% of the control) | 4 | 4 | 4 |
| ethyl | n-propyl | hydrogen | soybean | pre-emergent | Germination, % | 4 | 4 | 4 |
| | | | | | Height (% of the control) | 4 | 4 | 4 |
| | | | | | Dry weight (% of the control) | 4 | 2 | 4 |
| | | | | post-emergent | Germination, % | 4 | 4 | 2 |
| | | | | | Height (% of the control) | 4 | 4 | 4 |

TABLE 4-continued

| $R^3$ | $R^1$ | $R^2$ | Test plant | Test | | Dose, kg/ha | | |
|---|---|---|---|---|---|---|---|---|
| | | | | | | 1 | 3 | 5 |
| | | | | gent | Dry weight (% of the control) | 4 | 4 | 4 |

TABLE 5

| $R^3$ | $R^1$ | $R^2$ | Test plant | Test | | Dose, kg/ha | | |
|---|---|---|---|---|---|---|---|---|
| | | | | | | 1 | 3 | 5 |
| ethyl | hexamethylene | | maize | pre- | Germination, % | 2 | 4 | 2 |
| | | | | emer- | Height (% of the control) | 4 | 4 | 2 |
| | | | | gent | Dry weight (% of the control) | 2 | 4 | 2 |
| | | | | post- | Germination, % | 4 | 5 | 4 |
| | | | | emer- | Height (% of the control) | 5 | 4 | 2 |
| | | | | gent | Dry weight (% of the control) | 4 | 4 | 5 |
| | | | sunflower | pre- | Germination, % | 4 | 4 | 4 |
| | | | | emer- | Height (% of the control) | 4 | 4 | 4 |
| | | | | gent | Dry weight (% of the control) | 4 | 4 | 5 |
| | | | | post- | Germination, % | 5 | 4 | 4 |
| | | | | emer- | Height (% of the control) | 5 | 4 | 3 |
| | | | | gent | Dry weight (% of the control) | 4 | 3 | 3 |
| ethyl | hexamethylene | | soybean | pre- | Germination, % | 4 | 4 | 2 |
| | | | | emer- | Height (% of the control) | 4 | 4 | 3 |
| | | | | gent | Dry weight (% of the control) | 5 | 4 | 2 |
| | | | | post- | Germination, % | 4 | 2 | 4 |
| | | | | emer- | Height (% of the control) | 4 | 4 | 4 |
| | | | | gent | Dry weight (% of the control) | 4 | 5 | 5 |

TABLE 6

| $R^3$ | $R^1$ | $R^2$ | Test plant | Test | | Dose, kg/ha | | |
|---|---|---|---|---|---|---|---|---|
| | | | | | | 1 | 3 | 5 |
| ethyl | ethyl | hydrogen | sunflower | pre- | Germination, % | 5 | 4 | 5 |
| | | | | emer- | Height (% of the control) | 4 | 5 | 5 |
| | | | | gent | Dry weight (% of the control) | 4 | 4 | 5 |
| | | | | post- | Germination, % | 4 | 2 | 4 |
| | | | | emer- | Height (% of the control) | 4 | 4 | 4 |
| | | | | gent | Dry weight (% of the control) | 4 | 2 | 2 |
| | | | soybean | pre- | Germination, % | 4 | 4 | 4 |
| | | | | emer- | Height (% of the control) | 3 | 4 | 2 |
| | | | | gent | Dry weight (% of the control) | 5 | 4 | 2 |
| | | | | post- | Germination, % | 4 | 4 | 2 |
| | | | | emer- | Height (% of the control) | 4 | 4 | 4 |
| | | | | gent | Dry weight (% of the control) | 4 | 3 | 2 |

TABLE 7

| $R^3$ | $R^1$ | $R^2$ | Test plant | Test | | Dose, kg/ha | | |
|---|---|---|---|---|---|---|---|---|
| | | | | | | 1 | 3 | 5 |
| ethyl | methyl | hydrogen | sunflower | pre- | Germination, % | 4 | 4 | 4 |
| | | | | emer- | Height (% of the control) | 4 | 4 | 2 |
| | | | | gent | Dry weight (% of the control) | 4 | 4 | 2 |
| | | | | post- | Germination, % | 3 | 3 | 4 |
| | | | | emer- | Height (% of the control) | 4 | 4 | 4 |
| | | | | gent | Dry weight (% of the control) | 4 | 4 | 2 |
| | | | soybean | pre- | Germination, % | 4 | 4 | 4 |
| | | | | emer- | Height (% of the control) | 4 | 4 | 2 |
| | | | | gent | Dry weight (% of the control) | 4 | 4 | 2 |
| | | | | post- | Germination, % | 4 | 4 | 3 |
| | | | | emer- | Height (% of the control) | 4 | 4 | 4 |
| | | | | gent | Dry weight (% of the control) | 5 | 5 | 2 |

TABLE 8

| $R^3$ | $R^1$ | $R^2$ | Test plant | Test | | Dose, kg/ha | | |
|---|---|---|---|---|---|---|---|---|
| | | | | | | 1 | 3 | 5 |
| ethyl | morpholino | | maize | pre- | Germination, % | 4 | 4 | 4 |
| | | | | emer- | Height (% of the control) | 3 | 4 | 2 |
| | | | | gent | Dry weight (% of the control) | 4 | 4 | 2 |
| | | | | post- | Germination, % | 4 | 4 | 4 |
| | | | | emer- | Height (% of the control) | 4 | 3 | 3 |
| | | | | gent | Dry weight (% of the control) | 3 | 4 | 4 |
| | | | sunflower | pre- | Germination, % | 5 | 4 | 4 |
| | | | | emer- | Height (% of the control) | 4 | 4 | 4 |
| | | | | gent | Dry weight (% of the control) | 4 | 4 | 2 |
| | | | | post- | Germination, % | 4 | 3 | 4 |

TABLE 8-continued

| R³ | R¹ | R² | Test plant | Test | | | Dose, kg/ha | | |
|---|---|---|---|---|---|---|---|---|---|
| | | | | | | | 1 | 3 | 5 |
| ethyl | morpholino | soybean | | emer-<br>gent | Height (% of the control)<br>Dry weight (% of the control) | | 4<br>4 | 4<br>4 | 5<br>5 |
| | | | | pre-<br>emer-<br>gent | Germination, %<br>Height (% of the control)<br>Dry weight (% of the control) | | 4<br>2<br>4 | 4<br>2<br>2 | 3<br>2<br>2 |
| | | | | post-<br>emer-<br>gent | Germination, %<br>Height (% of the control)<br>Dry weight (% of the control) | | 2<br>4<br>5 | 4<br>3<br>4 | 4<br>2<br>2 |

TABLE 9

| R³ | R¹ | R² | Test plant | Test | | Dose, kg/ha | | |
|---|---|---|---|---|---|---|---|---|
| | | | | | | 1 | 3 | 5 |
| ethyl | allyl | allyl | sunflower | pre-<br>emer-<br>gent | Germination, %<br>Height (% of the control)<br>Dry weight (% of the control) | 3<br>4<br>4 | 4<br>4<br>4 | 4<br>3<br>5 |
| | | | | post-<br>emer-<br>gent | Germination, %<br>Height (% of the control)<br>Dry weight (% of the control) | 4<br>4<br>5 | 4<br>4<br>4 | 2<br>2<br>2 |
| | | | soybean | pre-<br>emer-<br>gent | Germination, %<br>Height (% of the control)<br>Dry weight (% of the control) | 4<br>4<br>4 | 4<br>4<br>4 | 3<br>2<br>1 |
| | | | | post-<br>emer-<br>gent | Germination, %<br>Height (% of the control)<br>Dry weight (% of the control) | 2<br>4<br>4 | 3<br>4<br>3 | 2<br>4<br>1 |

TABLE 10

| R³ | R¹ | R² | Test plant | Test | | Dose, kg/ha | | |
|---|---|---|---|---|---|---|---|---|
| | | | | | | 1 | 3 | 5 |
| ethyl | methyl | methyl | sunflower | pre-<br>emer-<br>gent | Germination, %<br>Height (% of the control)<br>Dry weight (% of the control) | 3<br>2<br>2 | 4<br>2<br>5 | 4<br>2<br>4 |
| | | | | post-<br>emer-<br>gent | Germination, %<br>Height (% of the control)<br>Dry weight (% of the control) | 4<br>2<br>4 | 2<br>2<br>4 | 4<br>2<br>4 |
| | | | soybean | pre-<br>emer-<br>gent | Germination, %<br>Height (% of the control)<br>Dry weight (% of the control) | 3<br>4<br>1 | 2<br>3<br>1 | 2<br>2<br>1 |
| | | | | post-<br>emer-<br>gent | Germination, %<br>Height (% of the control)<br>Dry weight (% of the control) | 1<br>2<br>1 | 2<br>3<br>1 | 1<br>2<br>1 |

The invention is elucidated in detail by the aid of the following non-limiting Examples.

EXAMPLE 1

A 10% solution of methyl 2-cyano-2-phenylacetate in benzene is saturated with ammonia under ice cooling. The reaction mixture is allowed to stand at room temperature for 2 hours, and then the product is filtered off. 2-Cyano-2-phenylacetic acid amide is obtained with a yield of 75%; m.p.: 148.5°–150° C.

EXAMPLE 2

A 10% solution of ethyl 2-cyano-2-ethyl-2-phenylacetate in ethanol is saturated with ammonia under cooling. The reaction mixture is allowed to stand at 5° C. for 96 hours, thereafter the solvent and the excess of ammonia are removed, and the product is filtered off. 2-Cyano-2-ethyl-2-phenylacetic acid amide is obtained with a yield of 80%; m.p.: 116.5°–117° C.

EXAMPLE 2

8.7 g (0.1 mole) of morpholine are dissolved in 20 ml of dry diethyl ether, and a solution of 10.5 g (0.05 mole) of 2-ethyl-2-phenyl-cyanoacetyl chloride in 20 ml of dry diethyl ether are added dropwise under cooling with ice (at a temperature below 10° C.). The reaction mixture is refluxed for 30 minutes, then cooled and washed with water. The organic phase is separated, washed in succession with 5% aqueous sodium carbonate solution, 2n aqueous hydrochloric acid and water, dried over magnesium sulfate, and evaporated. 11.4 g (89%) of 2-cyano-2-ethyl-2-phenylacetic acid morpholide are obtained; m.p.: 88°–90° C.

EXAMPLE 4

11 g of 2-cyano-2-ethyl-2-phenylacetyl bromide are added dropwise under cooling, at 20° to 30° C., to a solution of 3 g of n-propylamine and 4 g of pyridine in 20 ml of dry benzene. The reaction mixture is refluxed for 30 minutes and then processed as described in Example 3. 7.9 g (68.3%) of N-(n-propyl)-2-cyano-2-ethyl-2-phenylacetic acid amide are obtained; m.p.: 55°–56° C.

EXAMPLE 5

10.5 g (0.05 mole) of 2-cyano-2-ethyl-2-phenylacetyl chloride are dissolved in 50 ml of dichloromethane, the solution is cooled to 5° C., and 9.7 g (0.01 mole) of diallyl amine are added to it under maintaining the temperature of the mixture below 10° C. The reaction mixture is stirred at room temperature for 2 hours, then washed with water, dried over anhydrous magnesium sulfate, and the solvent is removed. 8.79 g (65.5%) of N,N-diallyl-2-cyano-2-ethyl-2-phenylacetic acid amide are obtained; m.p.: 33°–35° C.

EXAMPLE 6

4.4 g (0.05 mole) of morpholine are dissolved in 50 ml of methylene chloride, 20 ml of a 20% aqueous sodium hydroxide solution are added to it, and the mixture is cooled to a temperature below −10° C. with salted ice. 10.5 g (0.05 mole) of 2-cyano-2-ethyl-2-phenylacetyl chloride are added to the mixture in portions, under vigorous stirring. The reaction mixture is stirred at 0° C. for one hour, thereafter the phases are separated from each other, the organic phase is washed twice with dilute aqueous hydrochloric acid, dried over a mixture of anhydrous magnesium sulfate and potassium carbonate, filtered, and the solvent is evaporated. 10.3 g (81%) of 2-cyano-2-ethyl-2-phenylacetic acid morpholide are obtained; m.p.: 87°–89.5° C.

EXAMPLE 7

A solution of 9.75 g (0.05 mole) of 2-cyano-2-methyl-2-phenylacetyl chloride in 20 ml of acetone is cooled to 5° C., and a mixture of 5 g (0.05 mole) of cyclohexylamine, 5.2 g of triethyl amine and 10 ml of acetone is added to the solution under maintaining the temperature of the mixture below 10° C. The reaction mixture is poured into ice water, the separated solid is filtered off, and dried in vacuo. 12.12 g of N-cyclohexyl-2-cyano-2-methyl-2-phenylacetic acid amide are obtained; m.p.: 76°–78° C.

EXAMPLE 8

1 ml of pyridine is added to a solution of 0.05 mole of methyl 2-cyano-2-phenylacetate in 100 ml of toluene. The mixture is heated to boiling, and a solution of 0.05 mole of aniline in 50 ml of toluene is introduced under simultaneous removal of the condensation product (methanol) from the mixture by azeotropic distillation. After 3 hours of reaction the product separates from the mixture in crystalline form. 9.3 g (78%) of 2-cyano-2-phenylacetic acid anilide are obtained; m.p.: 134°–136° C.

EXAMPLE 9

Ethanolic sodium ethoxide solution is prepared from 23 g of dry ethanol and 2.3 g (0.1 g-atom) of metallic sodium. The resulting solution is heated to 50° C., and an ethanol solution of 23.6 g of 2-cyano-2-phenylacetic acid anilide is added, followed by 12 g (0.11 mole) of ethyl bromide. A precipitate separates from the solution. The mixture is refluxed until its pH reaches about 7 (this requires about 2 hours of boiling). The bulk of ethanol is removed, ice water is added to the residue in an amount necessary to dissolve the sodium bromide precipitate, and the mixture is extracted twice with 200 ml of benzene, each. The benzene solutions are combined, washed with cold 20% aqueous sodium hydroxide solution and then with aqueous hydrochloric acid, dried over a mixture of anhydrous magnesium sulfate and potassium carbonate, filtered, and the filtrate is evaporated. 17.1 g (65%) of 2-cyano-2-ethyl-2-phenylacetic acid anilide are obtained; m.p.: 110.4°–112.4° C. (after recrystallization from a mixture of ethanol and water).

EXAMPLES 10 TO 36

One proceeds as described in the previous Examples to obtain the compounds of the general formula (I) listed in Table 11 and characterized by their melting points and analytical data. The following methods are applied to prepare the individual compounds:

| End-product (No. of Example) | Method applied (No. of Example) |
| --- | --- |
| 10 to 14 | 1 |
| 15 to 28 | 2 |
| 29 and 32 to 36 | 8 |
| 30 and 31 | 9 |

The melting points listed in Table 11 were determined on a Koffler apparatus.

TABLE 11

| No. of example | $R^3$ | $R^1$ | $R^2$ | M.p. °C. | | Analysis Calculated C, H, N (%) | Found |
| --- | --- | --- | --- | --- | --- | --- | --- |
| 10 | hydrogen | hydrogen | hydrogen | 148.5–150 | C | 67.49 | 67.26 |
|  |  |  |  |  | H | 5.03 | 5.10 |
|  |  |  |  |  | N | 17.49 | 17.49 |
| 11 | methyl | hydrogen | hydrogen | 108.5–109.5 | C | 68.94 | 69.72 |
|  |  |  |  |  | H | 5.78 | 6.00 |
|  |  |  |  |  | N | 16.08 | 16.24 |
| 12 | methyl | ethyl | hydrogen | 41.5–54 | C | 71.26 | 71.38 |
|  |  |  |  |  | H | 6.98 | 7.14 |
|  |  |  |  |  | N | 13.85 | 13.46 |
| 13 | methyl | isopropyl | hydrogen | 58–64 | C | 72.19 | 72.21 |
|  |  |  |  |  | H | 7.46 | 7.47 |
|  |  |  |  |  | N | 12.95 | 13.05 |
| 14 | methyl | morpholino |  | 68.5–78 | C | 68.83 | 69.38 |
|  |  |  |  |  | N | 11.47 | 11.36 |
| 15 | ethyl | hydrogen | hydrogen | 116.5–117.5 | C | 70.1 | 69.90 |
|  |  |  |  |  | H | 6.42 | 6.89 |
|  |  |  |  |  | N | 14.88 | 15.20 |
| 16 | ethyl | methyl | hydrogen | 66.5–70 | C | 71.26 | 71.58 |
|  |  |  |  |  | H | 6.98 | 7.04 |
|  |  |  |  |  | N | 13.85 | 13.62 |
| 17 | ethyl | ethyl | hydrogen | 44.5–49 | C | 72.19 | 72.34 |
|  |  |  |  |  | H | 7.46 | 7.55 |
|  |  |  |  |  | N | 12.95 | 13.05 |
| 18 | ethyl | n-propyl | hydrogen | 57–60 | C | 72.69 | 73.63 |
|  |  |  |  |  | H | 8.28 | 8.26 |
|  |  |  |  |  | N | 12.11 | 12.51 |
| 19 | ethyl | isopropyl | hydrogen | 56.5–61 | C | 72.69 | 73.57 |

TABLE 11-continued

| No. of example | R³ | R¹ | R² | M.p. °C. | | Analysis Calculated C, H, N (%) | Found C, H, N (%) |
|---|---|---|---|---|---|---|---|
| | | | | | H | 8.28 | 8.08 |
| | | | | | N | 12.11 | 12.02 |
| 20 | ethyl | tert.-butyl | hydrogen | 38.5–42 | C | 73.73 | 73.97 |
| | | | | | H | 8.25 | 8.33 |
| | | | | | N | 11.47 | 11.37 |
| 21 | ethyl | 1,1-dimethyl-propinyl | hydrogen | 76.5–79 | C | 75.56 | 76.05 |
| | | | | | H | 7.13 | 7.35 |
| | | | | | N | 11.01 | 11.03 |
| 22 | ethyl | benzyl | hydrogen | 71.5–79 | C | 77.67 | 78.12 |
| | | | | | H | 6.52 | 6.13 |
| | | | | | N | 10.06 | 10.02 |
| 23 | ethyl | cyclohexyl | hydrogen | 75–77.2 | C | 75.52 | 76.46 |
| | | | | | H | 8.2 | 8.41 |
| | | | | | N | 10.36 | 10.21 |
| 24 | ethyl | methyl | methyl | 28.5–42 | C | 72.2 | 72.63 |
| | | | | | H | 7.46 | 7.67 |
| | | | | | N | 12.94 | 12.61 |
| 25 | ethyl | n-propyl | n-propyl | 35.5–41.5 | C | 74.96 | 75.19 |
| | | | | | H | 8.88 | 9.07 |
| | | | | | N | 10.28 | 10.25 |
| 26 | ethyl | allyl | allyl | 25–37 | C | 76.08 | 75.93 |
| | | | | | H | 7.51 | 7.63 |
| | | | | | N | 10.43 | 10.50 |
| 27 | ethyl | hexamethylene | | 57.5–64.5 | C | 75.52 | 75.61 |
| | | | | | H | 8.20 | 8.30 |
| | | | | | N | 10.63 | 10.50 |
| 28 | ethyl | morpholino | | 84.2–91 | C | 69.74 | 71.06 |
| | | | | | H | 7.03 | 7.17 |
| | | | | | N | 10.84 | 11.16 |
| 29 | hydrogen | phenyl | hydrogen | 134.4–136 | C | 76.25 | 77.30 |
| | | | | | H | 5.11 | 5.56 |
| | | | | | N | 11.85 | 11.84 |
| 30 | ethyl | phenyl | hydrogen | 110.4–112.4 | C | 77.25 | 77.86 |
| | | | | | H | 6.09 | 6.33 |
| | | | | | N | 10.59 | 10.88 |
| 31 | isopropyl | phenyl | hydrogen | 130.2–132.8 | C | 77.66 | 78.00 |
| | | | | | H | 6.54 | 6.69 |
| | | | | | N | 10.06 | 10.32 |
| 32 | hydrogen | 2-chloro-phenyl | hydrogen | 114–117 | C | 66.55 | 66.99 |
| | | | | | H | 4.09 | 4.38 |
| | | | | | N | 10.34 | 10.38 |
| | | | | | Cl | 13.09 | 13.31 |
| 33 | hydrogen | 4-chloro-phenyl | hydrogen | 151.8–153 | C | 66.55 | 65.81 |
| | | | | | H | 4.09 | 4.76 |
| | | | | | N | 10.34 | 9.96 |
| | | | | | Cl | 13.09 | 13.48 |
| 34 | hydrogen | 2,4-dichloro-phenyl | hydrogen | 152.8–155.4 | C | 59.04 | 58.46 |
| | | | | | H | 3.30 | 3.52 |
| | | | | | N | 9.18 | 3.93 |
| | | | | | Cl | 23.23 | 23.57 |
| 35 | hydrogen | 2,3-dichloro-phenyl | hydrogen | 150–151.4 | C | 59.04 | 59.01 |
| | | | | | H | 3.30 | 3.27 |
| | | | | | N | 9.18 | 8.79 |
| | | | | | Cl | 23.23 | 23.28 |
| 36 | hydrogen | 3,4-dichloro-phenyl | hydrogen | 143–145.5 | C | 59.04 | 58.83 |
| | | | | | H | 3.30 | 3.46 |
| | | | | | N | 9.18 | 8.93 |
| | | | | | Cl | 23.23 | 23.37 |

EXAMPLE 37

Preparation of a Wettable Powder

A compound described in any of Examples 1 to 36 is ground to a particle size of 1 to 20μ in an air-jet mill, and then homogenized with 3% by weight of Arkopon-T (sodium oleyl tauride) and 40% by weight of dolomite. A wettable powder with an active agent content of 57% is obtained, which can be diluted with water to obtain a spray liquid ready for use, containing 0.01 to 1.0% of active agent.

In the above process Arkopon-T and dolomite may also be applied in amounts of 1 to 5% and 20 to 60%, respectively. Instead of dolomite, kaoline or diatomaceous earth can also be applied as filling agent.

EXAMPLE 38

Preparation of a Wettable Powder

One proceeds as described in Example 37 with the difference that dolomite is applied in an amount of 30% calculated for the total weight of the composition, and 10% by weight of powdery sulfite waste liquor or whey powder are also added to the mixture. The latter additives improve the dispersibility of the powder and increase the adhesion of the composition to the plant surface in post-emergent applications.

EXAMPLE 39

Preparation of a Wettable Powder

A compound described in any of Examples 1 to 36 is homogenized with 5% by weight of Arkopon-T, calculated for the total weight of the composition. The resulting composition with an active agent content of 95% by weight can be diluted with water to obtain a spray liquid ready for use, containing 0.01 to 0.5% by weight of active agent.

For the purpose of post-emergent applications it is preferred to prepare wettable powders containing 80% by weight of active agent, 5% by weight of Arkopon-T and 15% by weight of whey powder.

EXAMPLE 40

Preparation of an Emulsifiable Concentrate

A compound described in any of Examples 1 to 36 is dissolved in a 3.5-fold amount of isophoron, and 1% by weight of Atlox 3400 B and 2% by weight of Atlox 4851 B, calculated for the weight of the solution, are added. The resulting emulsifiable concentrate can be diluted with water to obtain a spray liquid ready for use, containing 0.01 to 1.0% by weight of active agent.

EXAMPLE 41

Preparation of a Colloidal Suspension

A compound described in any of Examples 1 to 36 is ground to a particle size of 1 to 20μ. 45% by weight of the powdered active agent are admixed with 45% by weight of an organic solution (xylene, petrol or rape oil), and 10% by weight of a wetting agent is homogenized with this mixture (all pecentages being calculated for the total weight of the composition). The resulting colloidal suspension with an active agent content of 45% by weight can be diluted with water to obtain a spray liquid ready for use, containing 0.01 to 1% by weight of active agent.

EXAMPLE 42

Preparation of Microgranules

10% by weight, calculated for the total weight of the composition, of a compound described in any of Examples 1 to 36 are dissolved in acetone, and the solution is applied onto the surface of pearlite (particle size: 0.8 to 1 mm). The solvent is allowed to evaporate to obtain a microgranular composition with an active agent content of 10% by weight.

In the above process dolomite, coke or granulated corn cob can also be applied as carrier, instead of dolomite.

EXAMPLE 43

Preparation of a Composition for Seed Dressing or Film-coating 0.94% by weight, calculated for the total weight of the composition, of a compound described in any of Examples 1 to 36, are dissolved in acetone to form a 10% solution. The resulting solution is added to a stirred mixture of 47.24% of acetone, 3.93% of hydroxypropyl cellulose, 7.78% of polyethylene glycol and 31.56 % of water. If desired, a non-phytotoxic colouring agent can also be added to the mixture.

The mixture with the above composition can be applied onto the surface of seeds as a film coating. This operation can be performed in a conventional dragée-pan or in a fluidized-bed apparatus.

Film-coating can also be prepared so that a spray liquid is prepared from a wettable powder, emulsifiable concentrate or colloidal suspension described in any of Examples 37 to 41, 1% by weight of ultra-amylopectine is added to the resulting spray liquid as a film-forming agent, and seeds are coated with this mixture in an appropriate apparatus. If desired, a colouring agent can also be added to the spray liquid either before or after the introduction of the film-forming additive.

What we claim is:

1. A plant growth stimulating composition, comprising as active agent an effective amount of one or more compound(s) of the formula (I),

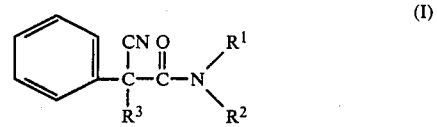

wherein
$R^1$ and $R^2$ each represent hydrogen atom, a $C_{1-5}$ alkyl group, a $C_{5-7}$ cycloalkyl group, a $C_6$–$C_{10}$ hydrocarbyl aryl group, a halogen-substituted $C_6$–$C_{10}$ hydrocarbyl aryl group, a $C_6$–$C_{12}$ hydrocarbyl aralkyl group, a $C_{2-5}$ alkenyl group or a $C_{2-5}$ alkynyl group, and
$R^3$ stands for hydrogen or a $C_{1-5}$ alkyl group, together with an inert solid, liquid and/or gaseous carrier or diluent, and optionally one or more inert additives.

2. A composition as set forth in claim 1, wherein the active agent is a compound of the formula (I) in which $R^1$ is hydrogen, $C_{1-3}$ alkyl, benzyl or allyl and $R^2$ is hydrogen, $C_{1-3}$ alkyl or allyl, and $R^3$ is a $C_{1-3}$ alkyl group.

3. A composition as set forth in claim 2, wherein the active agent is a compound of the formula (I), in which $R^1$ is hydrogen, methyl, ethyl, n-propyl, isopropyl or benzyl and $R^2$ is hydrogen, methyl or allyl, and $R^3$ is ethyl group.

4. A composition as set forth in claim 1, in the form of a wettable powder, an emulsifiable concentrate, a colloidal suspension, a microgranular formulation or a seed-dressing or film-forming mixture.

5. A composition as set forth in claim 1, in the form of a spray liquid ready for use, made by diluting a concentrate with water.

6. A compound of the formula (I), wherein $R^1$, $R^2$ and $R^3$ are as defined in claim 1, with the proviso that
(i) if $R^1$ is hydrogen, $R^2$ may not stand for hydrogen, $C_{1-3}$ alkyl, aralkyl or $C_{3-5}$ alkenyl, or
(ii) if both $R^1$ and $R^3$ are hydrogen, $R^2$ may not stand for aryl.

7. A composition as set forth in claim 1, wherein $R^1$ is n-propyl, $R^2$ is hydrogen and $R^3$ is ethyl.

8. A composition as set forth in claim 1, wherein $R^1$ and $R^2$ are hydrogen, and $R^3$ is ethyl.

9. A method of stimulating the growth of grop plants which comprises:
applying to the plants, the seeds of the plants or the soil in which such plants are grown an effective amount of a composition as defined in claim 1.

10. A method of stimulating the growth of crop plants which comprises:
applying to the plants, the seeds of the plants or the soil in which such plants are grown an effective amount of a composition as defined in claim 7.

11. A method of stimulating the growth of crop plants which comprises:
applying to the plants, the seeds of the plants or the soil in which such plants are grown an effective amount of a composition as defined in claim 8.

* * * * *